US006767725B2

(12) United States Patent
Bommarius et al.

(10) Patent No.: US 6,767,725 B2
(45) Date of Patent: Jul. 27, 2004

(54) ACETYL AMINO ACID RACEMASE FROM AMYCOLATOPSIS ORIENTALIS FOR RACEMIZING CARBAMOYL AMINO ACIDS

(75) Inventors: Andreas Bommarius, Atlanta, GA (US); Karlheinz Drauz, Freigericht (DE); Stefan Verseck, Hanau (DE); Maria-Regina Kula, Niederzier (DE)

(73) Assignee: Degussa AG, Duesseldorf (DE)

( * ) Notice: Subject to any disclaimer, the term of this patent is extended or adjusted under 35 U.S.C. 154(b) by 71 days.

(21) Appl. No.: 09/973,712

(22) Filed: Oct. 11, 2001

(65) Prior Publication Data

US 2002/0106752 A1 Aug. 8, 2002

(30) Foreign Application Priority Data

Oct. 11, 2000 (DE) .......................... 100 50 124

(51) Int. Cl.$^7$ ............................. C12P 13/04; C12N 9/90
(52) U.S. Cl. ........................ 435/106; 435/233; 435/280
(58) Field of Search ............................. 435/106, 233, 435/280

(56) References Cited

U.S. PATENT DOCUMENTS

| 4,981,799 | A | * | 1/1991 | Takahashi et al. | ........... | 435/233 |
| 5,525,501 | A | * | 6/1996 | Tokuyama et al. | ........... | 435/233 |
| 6,372,459 | B1 | | 4/2002 | Verseck et al. | ............. | 435/106 |

FOREIGN PATENT DOCUMENTS

| DE | 199 03 268 | 8/2000 |
| DE | 100 03 110 | 9/2000 |
| DE | 199 35 268 | 2/2001 |
| EP | 0 474 965 | 3/1992 |
| EP | 0 542 098 | 5/1993 |
| EP | 0 745 678 | 12/1996 |
| EP | 1 074 628 | 2/2001 |

OTHER PUBLICATIONS

Patent Abstracts of Japan, JP 2001–046088, Feb. 20, 2001.
S. Verseck, et al., Appl Microbiol Biotechnol, vol. 55, No. 3, XP–002202059, pp. 354–361, "Screening, Overexpression and Characterization of an N–Acylamino Acid Racemase from Amycolatopsis Orientalis Subsp.Lurida", Mar. 13, 2001.
Alberto Buson et al., Identification, Sequencing and Mutagenesis of the Gene for a D–Carbamoylase from Agrobacterium Radiobacter, FEMS Microbiology Letters, vol. 145 (1996) pp. 55–62.
Marina Otamiri et al., Complex Formation Between Chymotrypsin and Ethyl Cellulose as a Means to Solubilize the Enzyme in Active Form in Toluene, Biocatalysis, 1992, vol. 6, pp. 291–305.
Von Bhavender P. Sharma et al., Immobilisierte Biomaterialien—Techniken Und Anwendungen, Angew. Chem. 94, (1982) pp. 836–852.

Shinji Tokuyama et al., Purification and Properties of a Novel Enzyme, N–Acylamino Acid Racemase, from Streptomyces Atratus Y–53, Appl. Microbiol. Biotechnol. (1994) 40: 835–840.
Vikram M. Paradkar et al., Aqueous–Like Activity of α–Chymotrypsin Dissolved in Nearly Anhydrous Organic Solvents, J. Am. Chem. Soc., (1994), vol. 116, 5009–5010.
S. Tokuyama et al., Purification and Properties of Thermostable N–Acylamino Acid Racemase from Amycolatopsis sp. TS–1–60, Appl. Microbiol Biotechnol, (1995), vol. 42, pp. 853–859.
Oliver May et al., Inverting Enantioselectivity by Directed Evolution of Hydantoinase for Improved Production of L–Methionine, Nature Biotechnology, vol. 18, Mar. 2000, pp. 317–320.
Noriho Kamiya et al., Surfactant–Horseradish Peroxidase Complex Catalytically Active in Anhydrous Benzene, Biotechnology Techniques, vol. 11, No. 6, Jun. 1997, pp. 375–378.
Toshiaki Mori et al., A Variety of Lipid–Coated Glycoside Hydrolases as Effective Glycosyl Transfer Catalysts in Homogeneous Organic Solvents, Tetrahedron Letters, vol. 38, No. 11, pp. 1971–1974, 1997.
Beyer–Walter, Lehrbuch der organischen Chemie, S. Hirzel Verlag Stuttgart, 22nd edition, 1991, p. 822f.
Joo–Ho Park, et al., Production of D–Amino Acid Using Whole Cells of Recombinant Escherichia Coli with Separately and Coexpressed D–Hydantoinase and N–Carbamoylase, Biotechnol. Prog., (2000), vol. 16, pp. 564–570.
Burkhard Wilms et al., Cloning, Nucleotide Sequence and Expression of a New L–N–Carbamoylase Gene from Arthrobacter Aurescens DSM 3747 in E. coli, Journal of Biotechnology, vol. 68, (1999), pp. 101–113.
Yun–Peng Chao, et al., Production of D–p–Hydroxyphenylglycine by N–Carbamoyl–D–Amino Acid Amidohydrolase–Overproducing Escherichia Coli Strains, Biotechnol. Prog. (1999), vol. 15, pp. 603–607.
Nadine Batisse, et al., Two Amino Acid Amidohydrolase Genes Encoding L–Stereospecific Carbamoylase and Aminoacylase Are Organized in a Common Operon in Bacillus Stearothermophilus, Applied And Environmental Microbiology, Feb. 1997, vol. 63, No. 2, pp. 763–766.
Markus Pietzsch et al., Purification of Recombinant Hydantoinase and L–N–Carbamoylase from Arthrobacter Aurescens Expressed in Escherichia Coli: Comparison of Wild–Type and Genetically Modified Proteins, Journal of Chromatography B, 737 (2000), pp. 179–186.

* cited by examiner

Primary Examiner—Charles L. Patterson, Jr.
(74) Attorney, Agent, or Firm—Oblon, Spivak, McClelland, Maier & Neustadt, P.C.

(57) ABSTRACT

The invention relates to the use of the N-acetyl amino acid racemase from *Amycolatopsis orientalis* subspecies *lurida* for the racemiszation of N-carbamoyl amino acids. This use permits the 100% preparation of optically pure amino acids starting from racemic hydantoins in an enzymatic overall process.

19 Claims, No Drawings

SEQUENCE LISTING

<160> NUMBER OF SEQ ID NOS: 2

<210> SEQ ID NO 1
<211> LENGTH: 1107
<212> TYPE: DNA
<213> ORGANISM: Amycolatopsis orientalis
<220> FEATURE:
<221> NAME/KEY: CDS
<222> LOCATION: (1)..(1107)
<223> OTHER INFORMATION:

<400> SEQUENCE: 1

```
gtg aaa ctc agc ggt gtg gaa ctg cgc cgg gtc cgg atg ccg ctc gtg      48
Val Lys Leu Ser Gly Val Glu Leu Arg Arg Val Arg Met Pro Leu Val
1               5                   10                  15 gcc ccg ttc cgg acg tcg ttc ggg acg cag tcc gag cgg gaa ttg ctg      96
Ala Pro Phe Arg Thr Ser Phe Gly Thr Gln Ser Glu Arg Glu Leu Leu
                20                  25                  30 ctc gtc cgc gcg gtg acc ccg gcg ggc gag ggc tgg ggc gaa tgt gtc     144
Leu Val Arg Ala Val Thr Pro Ala Gly Glu Gly Trp Gly Glu Cys Val
            35                  40                  45 gcg atg gag gcg ccg ctc tac tcg tcg gag tac aac gac gcc gcc gag     192
Ala Met Glu Ala Pro Leu Tyr Ser Ser Glu Tyr Asn Asp Ala Ala Glu
        50                  55                  60 cac gtg ctg cgg aac cat ctg atc ccc gca ctg ctg gcg gcc gag gac     240
His Val Leu Arg Asn His Leu Ile Pro Ala Leu Leu Ala Ala Glu Asp
65                  70                  75                  80 gtg acc gcg cac aag gtg acg ccg ttg ctg gcg aag ttc aag ggc cac     288
Val Thr Ala His Lys Val Thr Pro Leu Leu Ala Lys Phe Lys Gly His
                85                  90                  95 cgg atg gcg aag ggc gcg ctg gag atg gcg gtc ctc gac gcc gaa ctc     336
Arg Met Ala Lys Gly Ala Leu Glu Met Ala Val Leu Asp Ala Glu Leu
                100                 105                 110 cgc gcg cat gac cgg tcc ttc gcg gcc gag ctg ggg tcc act cgc gac     384
Arg Ala His Asp Arg Ser Phe Ala Ala Glu Leu Gly Ser Thr Arg Asp
            115                 120                 125 tcc gtg gcc tgc ggg gtc tcg gtc ggg atc atg gac tcg atc ccg cac     432
Ser Val Ala Cys Gly Val Ser Val Gly Ile Met Asp Ser Ile Pro His
        130                 135                 140 ctg ctc gac gtc gtc ggc ggc tac ctc gac gag ggc tac gtc cgg atc     480
```

```
                                              -continued

Leu Leu Asp Val Val Gly Gly Tyr Leu Asp Glu Gly Tyr Val Arg Ile
145                 150                 155                 160 aag ctg aag atc gag ccc ggc tgg gac gtc gag ccg gtc cgg cag gtg        528
Lys Leu Lys Ile Glu Pro Gly Trp Asp Val Glu Pro Val Arg Gln Val
                165                 170                 175 cgt gag cgc ttc ggt gac gac gtg ctg ctg cag gtc gac gcg aac acc        576
Arg Glu Arg Phe Gly Asp Asp Val Leu Leu Gln Val Asp Ala Asn Thr
            180                 185                 190 gcg tac acg ctg ggc gac gcg ccc ctg ctg tcc cgg ctc gac ccg ttc        624
Ala Tyr Thr Leu Gly Asp Ala Pro Leu Leu Ser Arg Leu Asp Pro Phe
        195                 200                 205 gac ctg ctg ctg atc gag cag ccg ctc gaa gaa gag gac gtg ctc ggc        672
Asp Leu Leu Leu Ile Glu Gln Pro Leu Glu Glu Glu Asp Val Leu Gly
    210                 215                 220 cac gcc gag ctg gcc aag cgg atc cgg acg ccg atc tgc ctc gac gag        720
His Ala Glu Leu Ala Lys Arg Ile Arg Thr Pro Ile Cys Leu Asp Glu
225                 230                 235                 240 tcg atc gtc tcg gcc aag gcc gcc gcg gac gcg atc aag ctc ggc gcc        768
Ser Ile Val Ser Ala Lys Ala Ala Ala Asp Ala Ile Lys Leu Gly Ala
                245                 250                 255 tgc cag atc gtc aac atc aaa ccg ggc cgg gtc ggc gga tac ctc gaa        816
Cys Gln Ile Val Asn Ile Lys Pro Gly Arg Val Gly Gly Tyr Leu Glu
            260                 265                 270 gcc cgc cgg gtg cac gac gtc tgc gcg gca cac ggg atc gcg gtg tgg        864
Ala Arg Arg Val His Asp Val Cys Ala Ala His Gly Ile Ala Val Trp
        275                 280                 285 tgc ggc ggg atg atc gag acc ggg ctc ggc cgg gcg gcc aac gtc gca        912
Cys Gly Gly Met Ile Glu Thr Gly Leu Gly Arg Ala Ala Asn Val Ala
    290                 295                 300 ctg gcc tcg ctg ccc ggc ttc acg ctg ccg ggg gac acc tcg gcg tcc        960
Leu Ala Ser Leu Pro Gly Phe Thr Leu Pro Gly Asp Thr Ser Ala Ser
305                 310                 315                 320 ggc cgg ttc tat cgc acc gac atc acc gag ccg ttc gtg ctg gac gcc       1008
Gly Arg Phe Tyr Arg Thr Asp Ile Thr Glu Pro Phe Val Leu Asp Ala
                325                 330                 335 ggg cat ctg ccg gtg ccg acc ggg ccg ggc ctc ggg gtg act ccg att       1056
Gly His Leu Pro Val Pro Thr Gly Pro Gly Leu Gly Val Thr Pro Ile
            340                 345                 350 ccg gat ctt ctg gac gag gtc acc acg gag aaa gcg tgg atc ggt tcg       1104
Pro Asp Leu Leu Asp Glu Val Thr Thr Glu Lys Ala Trp Ile Gly Ser
        355                 360                 365 tag                                                                    1107

<210> SEQ ID NO 2
<211> LENGTH: 368
<212> TYPE: PRT
<213> ORGANISM: Amycolatopsis orientalis

<400> SEQUENCE: 2

Val Lys Leu Ser Gly Val Glu Leu Arg Arg Val Arg Met Pro Leu Val
1               5                   10                  15

Ala Pro Phe Arg Thr Ser Phe Gly Thr Gln Ser Glu Arg Glu Leu Leu
            20                  25                  30

Leu Val Arg Ala Val Thr Pro Ala Gly Glu Gly Trp Gly Glu Cys Val
        35                  40                  45

Ala Met Glu Ala Pro Leu Tyr Ser Ser Glu Tyr Asn Asp Ala Ala Glu
    50                  55                  60

His Val Leu Arg Asn His Leu Ile Pro Ala Leu Leu Ala Ala Glu Asp
65                  70                  75                  80
```

```
Val Thr Ala His Lys Val Thr Pro Leu Leu Ala Lys Phe Lys Gly His
            85              90              95
Arg Met Ala Lys Gly Ala Leu Glu Met Ala Val Leu Asp Ala Glu Leu
            100             105             110
Arg Ala His Asp Arg Ser Phe Ala Ala Glu Leu Gly Ser Thr Arg Asp
            115             120             125
Ser Val Ala Cys Gly Val Ser Val Gly Ile Met Asp Ser Ile Pro His
            130             135             140
Leu Leu Asp Val Val Gly Gly Tyr Leu Asp Glu Gly Tyr Val Arg Ile
145             150             155             160
Lys Leu Lys Ile Glu Pro Gly Trp Asp Val Glu Pro Val Arg Gln Val
            165             170             175
Arg Glu Arg Phe Gly Asp Asp Val Leu Leu Gln Val Asp Ala Asn Thr
            180             185             190
Ala Tyr Thr Leu Gly Asp Ala Pro Leu Leu Ser Arg Leu Asp Pro Phe
            195             200             205
Asp Leu Leu Leu Ile Glu Gln Pro Leu Glu Glu Glu Asp Val Leu Gly
    210             215             220
His Ala Glu Leu Ala Lys Arg Ile Arg Thr Pro Ile Cys Leu Asp Glu
225             230             235             240
Ser Ile Val Ser Ala Lys Ala Ala Ala Asp Ala Ile Lys Leu Gly Ala
            245             250             255
Cys Gln Ile Val Asn Ile Lys Pro Gly Arg Val Gly Gly Tyr Leu Glu
            260             265             270
Ala Arg Arg Val His Asp Val Cys Ala Ala His Gly Ile Ala Val Trp
            275             280             285
Cys Gly Gly Met Ile Glu Thr Gly Leu Gly Arg Ala Ala Asn Val Ala
            290             295             300
Leu Ala Ser Leu Pro Gly Phe Thr Leu Pro Gly Asp Thr Ser Ala Ser
305             310             315             320
Gly Arg Phe Tyr Arg Thr Asp Ile Thr Glu Pro Phe Val Leu Asp Ala
            325             330             335
Gly His Leu Pro Val Pro Thr Gly Pro Gly Leu Gly Val Thr Pro Ile
            340             345             350
Pro Asp Leu Leu Asp Glu Val Thr Thr Glu Lys Ala Trp Ile Gly Ser
            355             360             365
```

ACETYL AMINO ACID RACEMASE FROM AMYCOLATOPSIS ORIENTALIS FOR RACEMIZING CARBAMOYL AMINO ACIDS

BACKGROUND OF THE INVENTION

1. Field of the Invention

The present invention relates to the use of an N-acetylamino acid racemase (AAR) in a process for the racemization of N-carbamoyl amino acids.

2. Description of the Background

Optically pure amino acids are important starting materials for chemical synthesis and for parenteral nutrition. Many methods of preparing optically pure amino acids are known. Enzymatic processes, i.a. are suitable in this respect since, on the one hand, they operate catalytically and, on the other hand, permit the preparation of the amino acids with very high enantiomeric enrichment.

A known enzymatic process starts from racemic hydantoins which are transformed to N-carbamoyl-protected amino acids by means of hydantoinases. These are then converted by carbamoylases to the corresponding amino acids.

The separation of the racemates occurring in this reaction sequence takes place preferably on the basis of the N-carbamoyl-protected amino acids because both L- and D-selective carbamoylases are available (Park et al., Biotechnol. Prog. 2000, 16, 564–570; May et al., Nat Biotechnol. 2000, 18, 317–20: Pietzsch et al., J. Chromatogr. B Biomed. Sci. Appl. 2000, 737, 179–86; Chao et al., Biotechnol. Prog. 1999, 15, 603–7: Wilms et al., J. Biotechnol. 1999, 68, 101–13: Batisse et al., Appl. Environ. Microbiol. 1997, 63, 763–6; Buson et al., FEMS Microbiol. Lett. 1996, 145, 55–62, each of which is incorporated herein by reference).

In order to ensure complete conversion of the hydantoins used to optically pure amino acids, the necessary racemization has taken place hitherto on the basis of hydantoins by chemical or enzymatic means (EP 745678: EP 542098; Scheme 1).

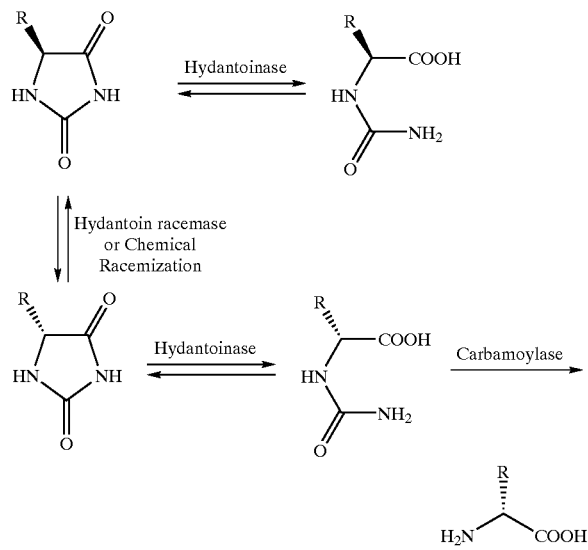

Scheme 1

N-acetyl amino acid racemases (AARs) from *Streptomyces atratus* Y-53 (Tokuyama et al., Appl. Microbiol. Biotechnol. 1994, 40, 835–840) and Amycolatopis sp. TS-1–60 (Tokuyama et al., App;. Microbiol. Biotechnol. 1995a, 42, 853–859) and *Amycolatopsis orientalis* sp. *lurida* (DE 19935268) are known. TS-1-60, however, is found to have a very low activity in the case of N-carbamoyl-protected amino acids. Moreover, this enzyme has the disadvantage of a very high metal ion dependence, which appears to be a drawback for the use of this enzyme in an industrial-scale process.

Accordingly, there remains a need for improved methods of racemizing N-carbamoyl amino acids which overcome the disadvantages described above.

SUMMARY OF THE INVENTION

The object of the present invention was, therefore, to show the use of an N-acetyl amino acid racemase for the improved racemization of N-carbamoyl amino acids compared to known methods. The intention was that this racemase might be used advantageously on an industrial scale in a process for the preparation of optically pure amino acid starting from racemic hydantoins.

It was another object of the present invention to provide a process for producing enantiomerically enriched amino acids.

The objects of the present invention, and others, may be accomplished with a method of racemizing N-carbamoyl amino acids, comprising:
  contacting an N-carbamoyl amino acid with an effective amount of an N-acetyl amino acid racemase (AAR) from *Amycolatopsis orientalis* subspecies *lurida*.

The objects of the present invention may also be accomplished with a method of producing enantiomerically enriched amino acids, comprising:
  contacting an N-carbamoyl amino acid with an effective amount of an N-acetyl amino acid racemase (AAR) from *Amycolatopsis orientalis* subspecies *lurida*, and
  contacting the racemized N-carbamoyl amino acid with a carbamoylase.

The objects of the present invention may also be accomplished with a method of producing enantiomerically enriched amino acids, comprising:
  contacting an a hydantoin with a hydantoinase to produce the corresponding N-carbamoyl amino acid,
  contacting an N-carbamoyl amino acid with an effective amount of an N-acetyl amino acid racemase (AAR) from *Amycolatopsis orientalis* subspecies *lurida* to produce a racemized N-carbamoyl amino acid, and
  contacting the racemized N-carbamoyl amino acid with a carbamoylase to produce the corresponding amino acid.

A more complete appreciation of the invention and many of the attendant advantages thereof will be readily obtained as the same becomes better understood by reference to the following detailed description below.

DETAILED DESCRIPTION OF THE INVENTION

Due to the fact that an N-acetyl amino acid racemase (AAR) from *Amycolatopsis orientalis* subspecies *lurida* (SEQ ID NO.: 2; the encoding nucleic acid sequence is shown in SEQ ID NO.: 1) is used in a process for the racemization of N-carbamoyl amino acids, and in view of the surprisingly high activity of the AAR used according to the invention compared with TS-1–60 in terms of the racemization of N-carbamoyl amino acids, it is possible to achieve an equilibrium of enantiomers of N-carbamoyl-protected amino acids in an improved process.

This is particularly advantageous in that it is thus possible to establish a further enzymatic step in a process for the preparation of optically pure amino acids which is based on hydantoins (Scheme 2).

Scheme 2

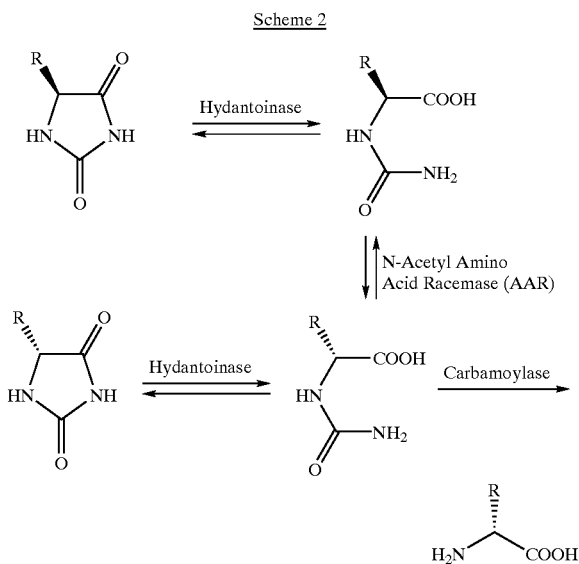

In contrast to the enzymatic processes known from the literature and which proceed by way of enzymatic or optionally stressing chemical racemization of hydantoins (Scheme 1), a further advantageous possibility of generating optically pure amino acids from racemic hydantoins has thus been created.

The variant of AAR from *Amycolatopsis o*. sp. *lurida* prepared by recombinant technology according to DE 19935268, incorporated herein by reference, is preferably used for the racemization process. It is known from DE 19935268 that this exhibits relatively little heavy metal ion dependence (particularly with regard to cobalt ions) and has low amino acid inhibition. The generation thereof as a recombinant enzyme is also explained therein.

The process according to the invention, as has been mentioned, is used advantageously in an overall process for the preparation of enantiomerically enriched amino acids or derivatives thereof starting from hydantoins or N-carbamoyl amino acids. In the case of hydantoins, it is preferable to proceed in such a manner that racemic hydantoins are cleaved by hydantoinases into the corresponding racemic N-carbamoyl amino acids and these are then converted by L- or D-specific carbamoylases into the optically active L- or D-amino acids. To ensure that no enrichment of the unconverted enantiomer of an N-carbamoyl amino acid takes place in the reaction mixture, the enantiomers of the N-carbamoyl amino acids are brought into equilibrium by the addition of the AAR according to the invention and it is thus likewise possible to convert the racemic hydantoin wholly to optically pure amino acids.

The process of the present invention is preferably conducted in an enzyme-membrane reactor. Such a reactor is described in, for example, DE 199 10 691.6, incorporated herein by reference.

The enzymes mentioned may be used together or successively in the free form as homogeneously purified compounds or as enzymes prepared by recombinant technology.

Moreover, the enzymes may also be used as a constituent of a guest organism (whole-cell catalyst as described in U.S. patent application Ser. No. 09/407,062, incorporated herein by reference) or in conjunction with the digested cell mass of the host organism. It is also possible to use the enzymes in the immobilized form (Bhavender P. Sharma, Lorraine F. Bailey and Ralph A. Messing, "Immobilisierte Biomaterialiern—Techniken and Anwendungen", Angew. Chem. 1982, 94, 836–852, incorporated herein by reference). Immobilization takes place advantageously by freeze-drying (Dordick et al. J. Am. Chem. Soc. 194, 116, 5009–5010, incorporated herein by reference; Okahata et al. Tetrahedron Lett. 1997, 38, 1971–1974, incorporated herein by reference; Adlercreutz et al. Biocatalysis 1992, 6, 291–305, incorporated herein by reference). Freeze-drying in the presence of surfactant substances such as Aerosol OT or polyvinyl pyrrolidone or polyethylene glycol (PEG) or Brij 52 (diethylene glycol-mono-cetylether) (Goto et al. Biotechnol. Techniques 1997, 11, 375–378, incorporated herein by reference) is more particularly preferred.

The microorganism *Amycolatopsis orientalis* subsp. *lurida* has been deposited with the German Collection for Microorganisms under the accession number DSM43134.

The term "AAR" as used herein refers both the native enzyme and the enzyme prepared by recombinant technology.

The term "enantiomerically enriched" denotes the presence of one enantiomer in the mixture with the other in a proportion of >50%. The proportion, of course, may be higher, such as, for example, $\geq 60\%$, $\geq 75\%$, $\geq 80\%$, $\geq 90\%$, $\geq 95\%$, $\geq 98\%$, or $\geq 99\%$.

The term "amino acid" within the context of the present invention means a natural or unnatural α-amino acid, i.e., the radical situated on the α-C-atom of the α-amino acid may be derived from a natural amino acid as described in Beyer-Walter, Lehrbuch der organischen Chemie, S. Hirzel Verlag Stuttgart, 22nd edition, 1991, p.822f., incorporated herein by reference or also from corresponding α-radicals of unnatural amino acids which are listed, e.g. in DE 19903268.8, incorporated herein by reference.

EXAMPLES

Having generally described this invention, a further understanding can be obtained by reference to certain specific examples which are provided herein for purposes of illustration only and are not intended to be limiting unless otherwise specified.

Detection of Racemase Activity of a Recombinant AAR Enzyme

The substrate spectrum of the N-acetyl amino acid racemase from *Amycolatopsis orientalis* subsp. *lurida* was tested using the enzyme assay described below.

The assay was composed of the following:

| | |
|---|---|
| Tris/HCl buffer | 50 mM (pH 8.0) |
| Substrate | 25 mM |
| Cobalt chloride | 6 mM |
| AAR | approx 150 µg purified protein |
| Final volume | 1 ml |

Enantiomerically pure amino acid derivatives were used in the test and the formation of the corresponding racemate was monitored in the polarimeter (Perkin-Elmer 241).

Incubation took place at 30° C. (heated cell) for 3 to 12 hours. The measurements were taken at a wave length of λ=365 nm.

TABLE 1

List of the substrates tested and of the corresponding specific activity of the AAR.

| Substrate | Specific activity |
| --- | --- |
| N-Carbamoyl-D-Met | 155 mU/mg |
| N-Carbamoyl-D-Phe | 20 mU/mg |
| N-Carbamoyl-L-Abs | 15 mU/mg |
| N-Carbamoyl-L-Leu | 20 mU/mg |
| N-Carbamoyl-L-Met | 118 mU/mg |
| N-Carbamoyl-L-Tyr | 62 mU/mg |
| N-Carbamoyl-L-Val | 20 mU/mg |

The N-acyl amino acid racemase from A. TS-1–60 with N-carbamoyl-D-Met as substrate has an activity of 100 mU/mg. This specific activity is thus 35% lower than that of the racemase from *A. orientalis* subsp. *lurida*.

Obviously, numerous modifications and variations of the present invention are possible in light of the above teachings. It is therefore to be understood that within the scope of the appended claims, the invention may be practiced otherwise than as specifically described herein.

This application is based on German Patent Application serial No. 100 50 124.9, filed on Oct. 11, 2000, which is incorporated herein by reference.

What is claimed is:

1. A method of racemizing N-carbamoyl amino acids, comprising:
contacting an N-carbamoyl amino acid with an effective amount of an N-acetyl amino acid racemase (AAR) from *Amycolatopsis orientalis* subspecies *lurida*.

2. The method of claim 1, which is conducted in an enzyme-membrane reactor.

3. The method of claim 1, wherein the N-acetyl amino acid racemase has the amino acid sequence shown in SEQ ID) NO: 2.

4. The method of claim 1, wherein the N-carbamoyl amino acid is an N-carbamoyl α-amino acid.

5. The method of claim 1, wherein the N-carbamoyl amino acid is a natural N-carbamoyl amino acid.

6. The method of claim 1, wherein the N-carbamoyl amino acid is an unnatural N-carbamoyl amino acid.

7. The method of claim 1, further comprising treating the racemized N-carbamoyl amino acid with a carbamoylase.

8. A method of producing enantiomerically enriched amino acids, comprising:
contacting an N-carbamoyl amino acid with an effective amount of an N-acetyl amino acid racemase (AAR) from *Amycolatopsis orientalis* subspecies *lurida*, and contacting the racemized N-carbamoyl amino acid with a carbamoylase.

9. The method of claim 8, which is conducted in an enzyme-membrane reactor.

10. The method of claim 8, wherein the N-acetyl amino acid racemase has the amino acid sequence shown in SEQ ID NO: 2.

11. The method of claim 8, wherein the N-carbamoyl amino acid is an N-carbamoyl α-amino acid.

12. The method of claim 8, wherein the N-carbamoyl amino acid is a natural N-carbamoyl amino acid.

13. The method of claim 8, wherein the N-carbamoyl amino acid is an unnatural N-carbamoyl amino acid.

14. A method of producing enantiomerically enriched amino acids, comprising:

contacting a hydantoin with a hydantoinase to produce the corresponding N-carbamoyl amino acid, contacting an N-carbamoyl amino acid with an effective amount of an N-acetyl amino acid racemase (AAR) from *Amycolatopsis orientalis* subspecies *lurida* to produce a racemized N-carbamoyl amino acid, and contacting the racemized N-carbamoyl amino acid with a carbamoylase to produce the corresponding amino acid.

15. The method of claim 14, which is conducted in an enzyme-membrane reactor.

16. The method of claim 14, wherein the N-acetyl amino acid racemase has the amino acid sequence shown in SEQ ID NO: 2.

17. The method of claim 14, wherein the N-carbamoyl amino acid is an N-carbamoyl α-amino acid.

18. The method of claim 14, wherein the N-carbamoyl amino acid is a natural N-carbamoyl amino acid.

19. The method of claim 14, wherein the N-carbamoyl amino acid is an unnatural N-carbamoyl amino acid.

* * * * *